(12) United States Patent
Swofford

(10) Patent No.: US 9,131,955 B2
(45) Date of Patent: Sep. 15, 2015

(54) ANESTHESIA IN BONE JOINTS

(75) Inventor: John Swofford, Fortville, IN (US)

(73) Assignee: Swofford Ideas, LLC, Fishers, IN (US)

( * ) Notice: Subject to any disclaimer, the term of this patent is extended or adjusted under 35 U.S.C. 154(b) by 326 days.

(21) Appl. No.: 13/354,506

(22) Filed: Jan. 20, 2012

(65) Prior Publication Data

US 2013/0190614 A1    Jul. 25, 2013

(51) Int. Cl.
*A61M 5/158* (2006.01)
*A61M 19/00* (2006.01)
*A61B 17/34* (2006.01)
*A61B 5/00* (2006.01)
*A61M 21/02* (2006.01)

(52) U.S. Cl.
CPC .......... *A61B 17/3401* (2013.01); *A61B 5/4571* (2013.01); *A61M 21/02* (2013.01); *A61M 19/00* (2013.01)

(58) Field of Classification Search
CPC .. A61B 17/3401; A61M 19/00; A61M 5/001; A61K 9/0085; A61K 9/127
USPC .................................. 604/512, 264, 272, 506
See application file for complete search history.

(56) References Cited

U.S. PATENT DOCUMENTS

| | | | |
|---|---|---|---|
| 4,128,351 A | 12/1978 | Kurtz et al. | |
| 4,490,139 A | 12/1984 | Huizenga et al. | |
| 5,292,310 A | 3/1994 | Yoon | |
| 5,733,266 A | 3/1998 | Gravlee, Jr. | |
| 5,788,679 A | 8/1998 | Gravlee, Jr. | |
| 5,843,048 A * | 12/1998 | Gross | 604/264 |
| 6,075,059 A * | 6/2000 | Reader | 514/738 |
| 6,752,769 B2 | 6/2004 | Alberico | |
| 7,591,807 B2 | 9/2009 | Villette | |
| 7,635,353 B2 | 12/2009 | Gurusamy et al. | |
| 7,824,382 B2 | 11/2010 | Reihl | |
| 2002/0006904 A1* | 1/2002 | Dunn | 514/12 |
| 2006/0200095 A1 | 9/2006 | Steube | |
| 2009/0171192 A1* | 7/2009 | Patrick et al. | 600/424 |
| 2011/0264229 A1* | 10/2011 | Donner | 623/18.11 |

OTHER PUBLICATIONS

Cohen; Sacroiliac Joint Pain: A Comprehensive Review of Anatomy, Diagnosis, and Treatment; 2005; Anesthesia and Analgesia; vol. 101; pp. 1440-1453.*
Cohen, Anesthesia and Analgesia, 2005, vol. 101, pp. 1440-1453.*
Malamed, Handbook of Local Anesthesia, 6th Edition, Chapter 14, p. 1, 2012
Malamed, Handbook of Local Anesthesia, 6th Edition, Chapter 14, p. 14, 2012.

* cited by examiner

*Primary Examiner* — Bhisma Mehta
*Assistant Examiner* — William Frehe
(74) *Attorney, Agent, or Firm* — Woodard, Emhardt, Moriarty, McNett & Henry LLP

(57) ABSTRACT

A medical needle, kit, and pharmacological composition of matter comprising a local anesthetic pertaining to inserting a needle percutaneously in a patient is disclosed. A method is disclosed with the needle having a leading apex that is dulled to restrict penetration through articular cartilage, advancing the needle leading apex into a bone joint and stopping said needle leading apex short of substantially penetrating bone joint articular cartilage, and injecting through the needle lumen a pharmacological composition of matter comprising a local anesthetic and out of said opening and into the bone joint to contribute to the anesthetizing of nerves near said bone joint.

13 Claims, 25 Drawing Sheets

ANESTHESIA IN BONE JOINTS

BACKGROUND

The present invention relates generally to anesthesia, and more specifically to a device, kit, and method of applying local anesthesia, particularly regarding bone joints.

Anesthesia is generally broken down into general anesthesia and local anesthesia. Application of local anesthesia not only have therapeutic uses, but also may have diagnostic uses. For example, injecting local anesthesia in bone joints has been employed diagnostically for confirming or refuting a medical hypothesis that a certain form of pain, is caused by, or at least correlated with, localized nerves at a given joint. By injecting a contrast agent and/or a localized anesthetic at the joint, if the patient's pain is eliminated, or at least reduced, this is a "positive" indication that the medical hypothesis is correct, thereby indicating a subsequent medical therapeutic treatment at or pertaining to such joint. For example, such therapeutic treatment might include fusion (by surgical implant or otherwise) at the joint. Therapeutic treatment may also (and/or instead of) employ injectables via the present needle, including for example steroids, stem cells, glucose, hyaluronidase, and/or otherwise. However, prior to such therapy, the physician wants to confirm the hypothesis that nerves at or near the joint are the problem. As such, by injecting local anesthetic at the joint, this is further confirmation of that hypothesis.

However, precisely injecting a local anesthesia in such joint is difficult. Moreover, the bone joint surface tissues, typically articular cartridge, may be delicate and can be damaged. Moreover, such damage may be irreversible, or at least difficult to reverse or heal. For example, prior needles 10, with sharp tapered tips, have been inserted through the skin 707 and missing the joint, penetrating into bone 901 (FIG. 1A); and/or entering the joint but penetrating the articular cartilage 903 (FIG. 1B) of the joint.

Thus, there is a long felt need for providing accurate diagnostics of such bone joint-nerve hypothetical diagnoses, and providing it in an easier, more reliable and/or less damaging manner.

SUMMARY

The present inventions are defined by the claims, and only the claims. In summary, this may include the needle, kit, and pharmacological composition of matter comprising a local anesthetic pertaining to inserting a needle percutaneously in a patient, the needle having a leading apex that is dulled to restrict penetration through articular cartilage, advancing the needle leading apex into a bone joint and stopping said needle leading apex short of substantially penetrating bone joint articular cartilage, and injecting through the needle lumen a pharmacological composition of matter comprising a local anesthetic and out of said opening and into the bone joint to contribute to the anesthetizing of nerves near said bone joint.

Further forms, objects, features, aspects, benefits, advantages, and embodiments of the present invention will become apparent from a detailed description and drawings provided herewith.

DESCRIPTION OF THE SELECTED EMBODIMENTS

Figure 1A:
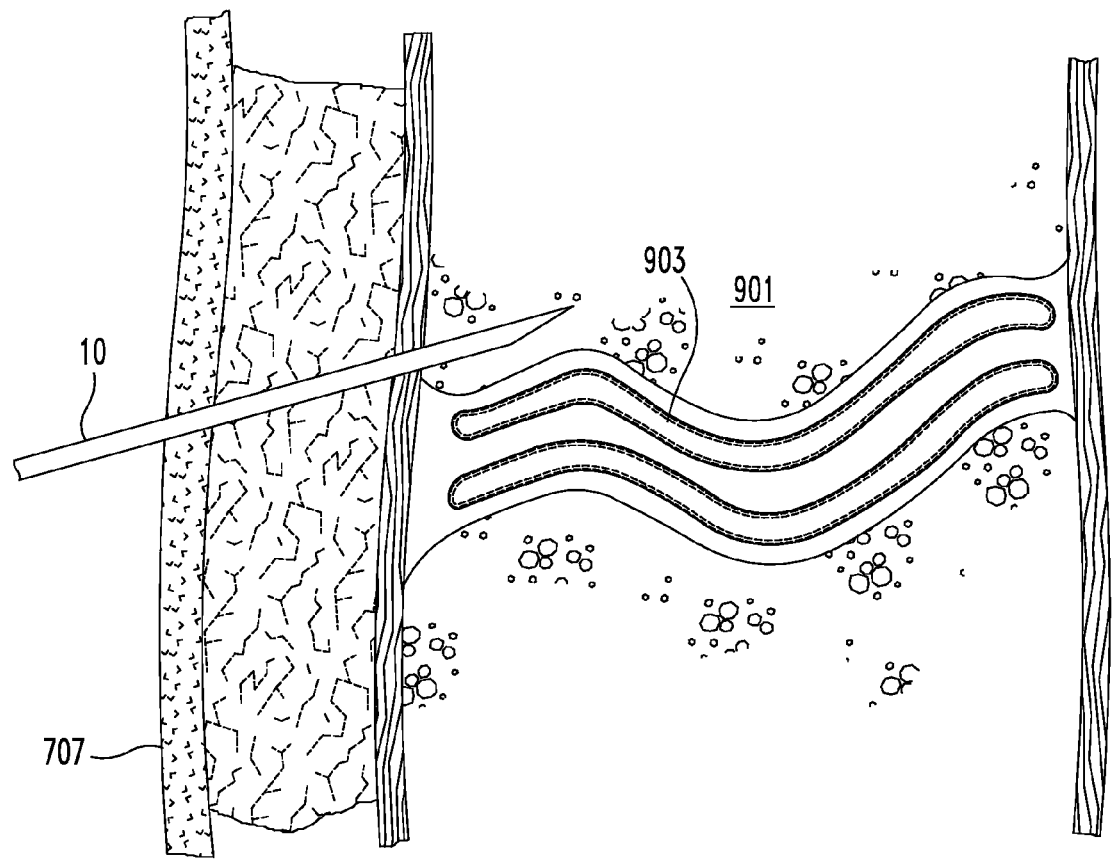
FIGS. 1A and 1B show prior art needles penetrating bone and/or articular cartilage.
Figure 1B:
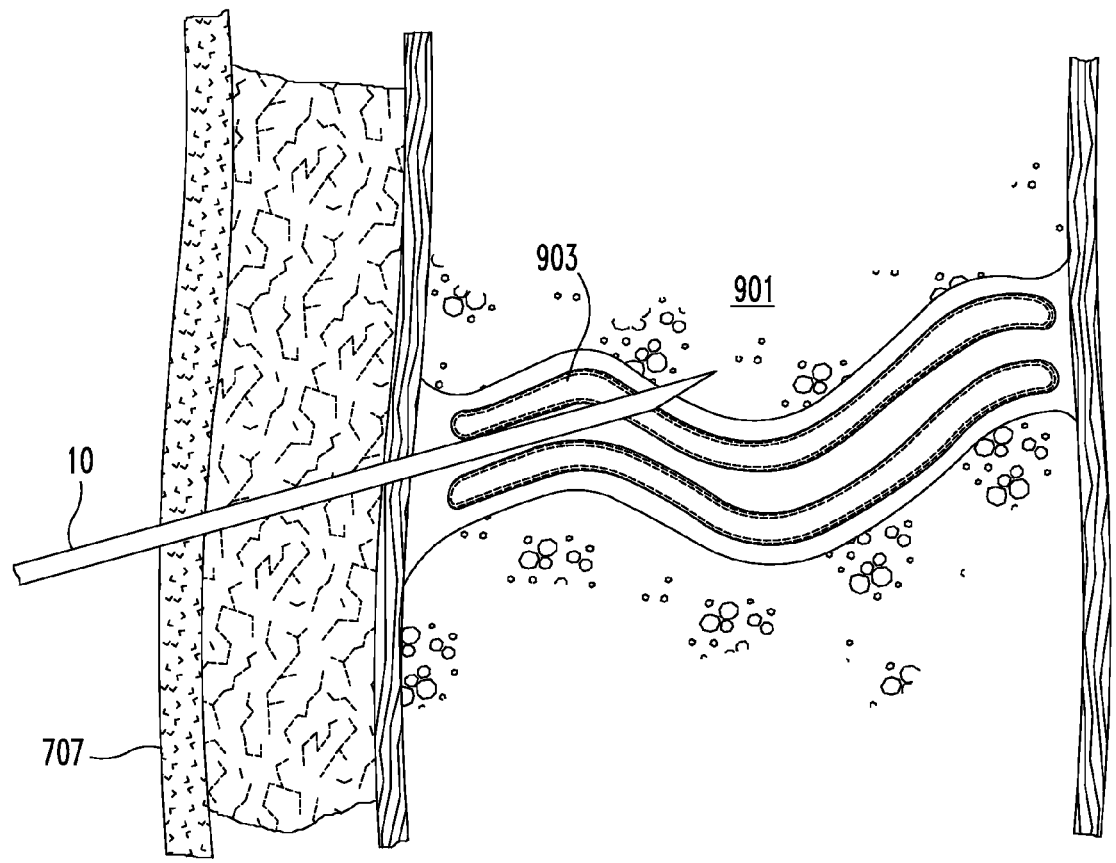
Figure 2A:
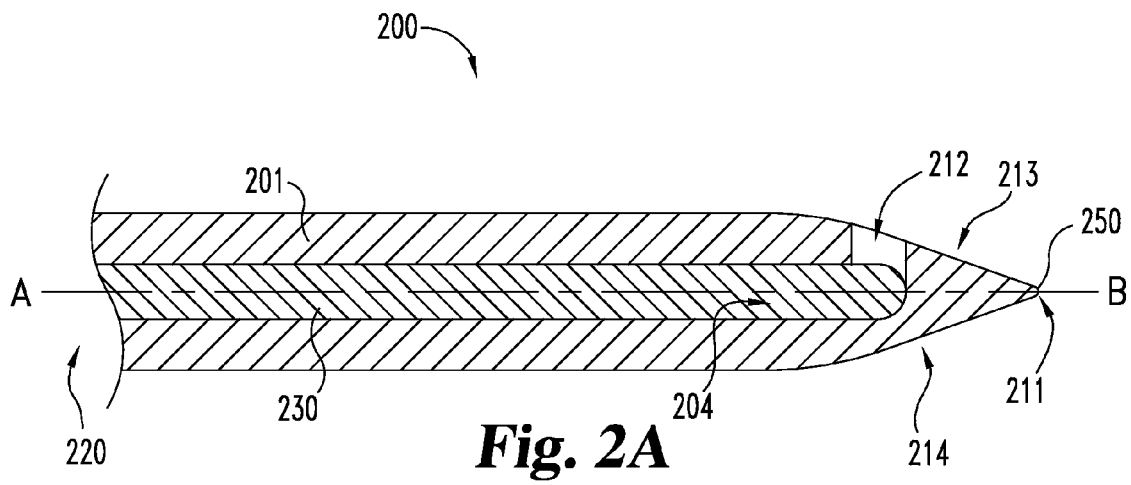
FIGS. 2A-2G show a first example of a the ends of needle, with 2A a full section view, 2B a side elevation view, 2C a front view, 2D like 2A but with a stylet partially withdrawn, 2E like 2A but without a stylet, and 2F (side) and 2G (distal end view) with the distal tip of the needle bent.
Figure 2B:
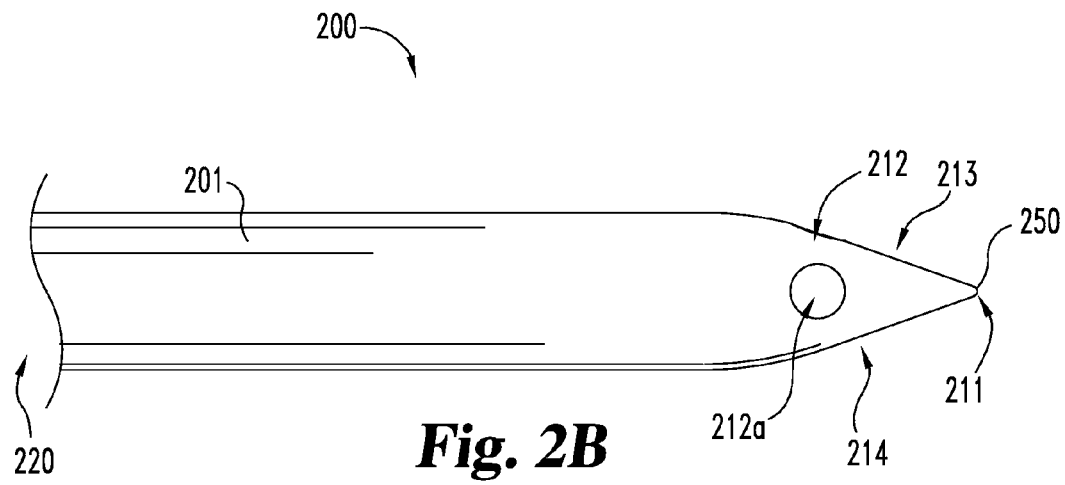
Figure 2C:
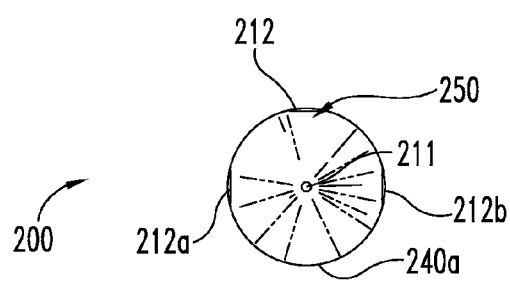
Figure 2D:
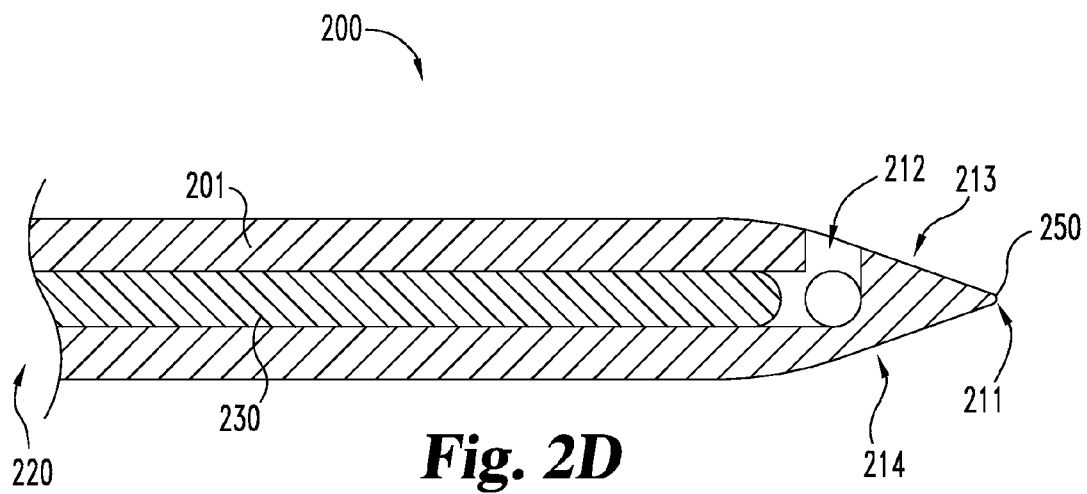
Figure 2E:
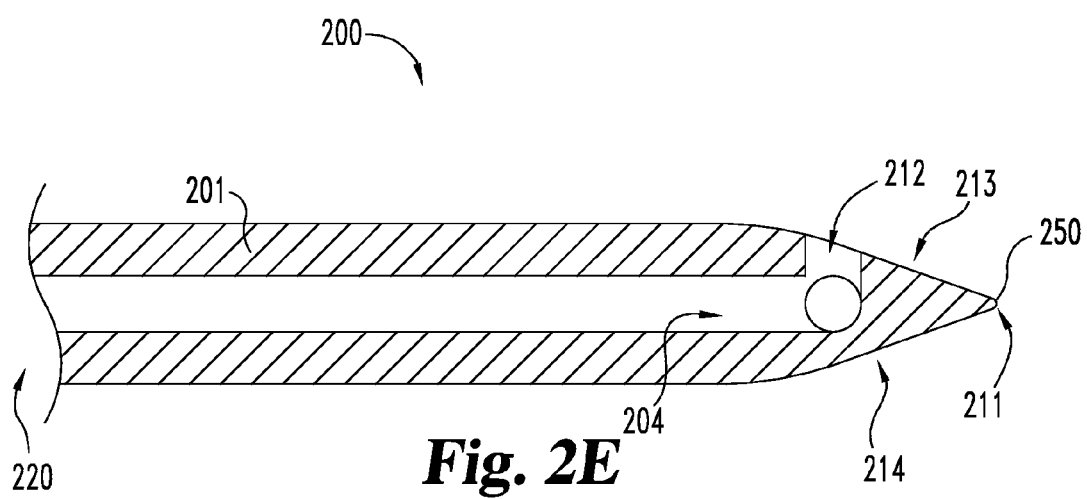
Figure 2F:
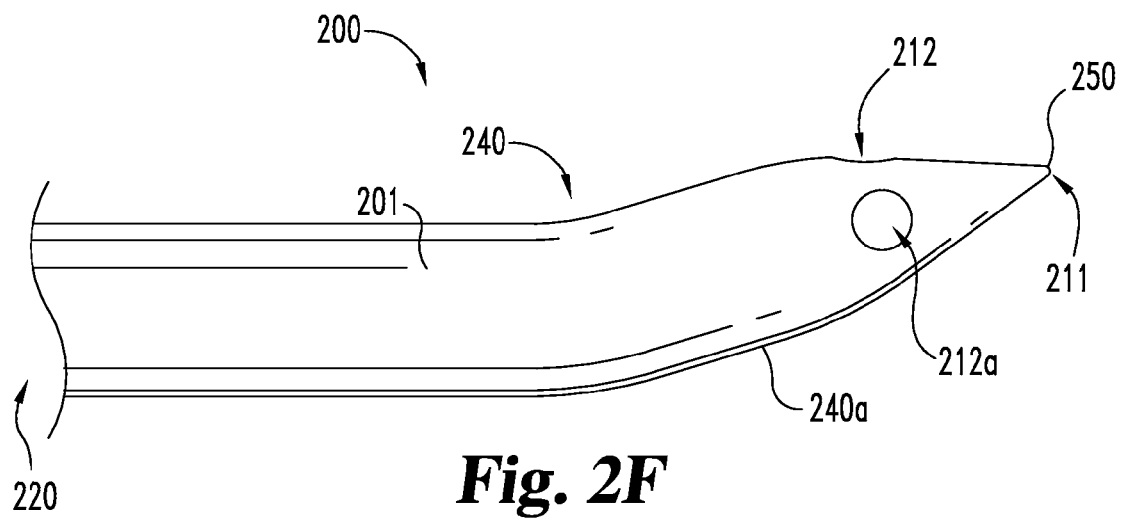
Figure 2G:
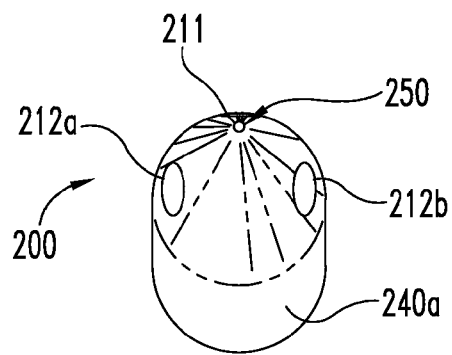

For the purpose of promoting an understanding of the principles of the invention, reference will now be made to the embodiments or examples illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

FIGS. 1-9C show mere examples of that which is claimed. Those examples are described here. As used in the claims and the specification, the following terms have the following defined meanings:

The term "advancing" means moving forward or in a direction proximal to distal.

The term "along a common radius" means in relative terms two or more points on a common line which is in a radial direction from one point to another point. For example, a radius may lie perpendicular to a longitudinal axis and radially outward towards the outer surface of a needle when viewed from viewed from a front view.

The term "anesthetizing nerves" means causing nerve to have their sensory indication of pain eliminated or at least reduced.

The term "articular cartilage" means cartilage between bone at a bone joint.

The term "attachment means" means is a mechanical interface to attach one component to another. This may include screw threads (male and female), snap fits, bayonet mounts, friction fits, third piece locking members and other known mechanisms for attaching to needles.

The term "blocking cartilage and/or bone tissue" means using some solid structure or part of a structure to prevent the patient's cartilage, the patient's bone, fragments thereof, and/or any combination thereof from being forced into an opening.

The term "bone joint" is the anatomical location in a patient between two adjacent bones. This may include synarthrosis joints (athough in this context this would be rare), fibrous joints, amphiarthrosis joints, cartilaginous joints, diarthrosis joints, synovial joints, simple joint, compound joint, complex joint, articulations of hand, elbow joints, wrist joints, axillary articulations, sternoclavicular joints, vertebral articulations, temporomandibular joints, sacroiliac joints, hip joints, knee joints and articulations of foot.

The term "clogging" means to fill, or at least partially fill, an opening and or lumen so as to substantially prevent, or at least substantially impede, the flow of liquids.

The term "collateral region" means a portion of a patient's anatomy separate from another portion of their anatomy (although they may be partially overlapping) in which pain or discomfort manifests itself even though the cause is located elsewhere. For example, pain in the lower back may be a collateral region from pain that is caused at the sacral iliac joint. Collateral regions, in this context, most commonly occur where a nerve that is causing pain is located elsewhere than where the pain seems to manifest itself to the patient.

The term "container" means any bag, box, tray (covered or otherwise) for containing one or more other items. Frequently but optionally, in this context, the container interior is either surgically sterile and or surgically sterilizable.

The term "contrast agent" means a liquid injectable composition of matter which aids in the visualization of an anatomical structure. This may include fluoroscopic contrast media, radiographic contrast media, MRI contrast media, ultrasonic contrast media and otherwise.

The term "contribute" means to add, increase or enhance the effect of something else or of a desired result.

The term "deflected off" means bent or otherwise formed or deformed with respect to an axis.

The term "diagnosing" means the identification of the nature and cause of pain or other medical problem.

The term "dulled" means rounded, flattened or otherwise altered geometry of a point and/or an edge of a material (e.g. stainless steel, titanium, plastic, ceramic) as compared to that material's ability to otherwise hold an edge or point.

The term "injecting" means to force a fluid under pressure from one location to another.

The term "inner surface of said lumen" means the inner most solid surface within a needle defining all, or at least substantially most, of a lumen. Ordinarily it is generally cylindrical in shape (although may be of other cross-sections, square, triangular, etc.).

The term "kit" means two or more components (medical device and or pharmacological compositions of matter) packaged together (in a container or otherwise).

The term "leading apex" means the forward most (or most distal) point of a needle. This may be a point and or an edge (to the extent an edge has more than one point equally distal) or a surface (to the extent an edge surface has more than one point equally distal). It may be of the needle body, or stylet, or both, or otherwise.

The term "liquid injection means" means is a device, such as a syringe, pump, bulb or otherwise, which can impart pressure on a fluid to cause injecting.

The term "local anesthetic" means a pharmacological composition of matter, much commonly in liquid form, which anesthetizes nerves in a locality where it is administered, as opposed to a gereral anestetic which, among other things, is normally injected into the blood stream and causes a patient to lose consciousness.

The term "lower back pain" means patient pain which is perceived in the lumbar region of the spine.

The term "lumen extending" means the general direction, such as a longitudinal axis, in which a lumen runs.

The term "major longitudinal axis" means an axis running down the longitudinal center of a needle. Commonly, this is located in free space at or near the center of the lumen, although not necessarily so. Most commonly, it is linear, although if a needle is curved then it is correspondingly curvilinear.

The term "medical indication" means the governmentally approved or cleared medical use of a kit, device and/or a pharmacological composition of matter and/or combination thereof.

The term "near said bone joint" means sufficiently anatomically close to a bone joint such that a local anestetic causes anestizing of nerves.

The term "opening near a distal end" means at or within about one centimeter or the leading apex.

The term "orthopedic implant" means any man-made implant, whether metal (stainless steel, titanium or otherwise), ceramic, plastic, hybrid otherwise to attach to or otherwise fuse bone, and may also include fixation devices which are partially internal and partially external.

The term "orthopedic screw" means an orthopedic implant having one or more threads to screw into cortical or cancellous bone. This includes orthopedic pins with such threads.

The term "outer surface of said needle" means the inner most solid surface on the outside of a needle. Ordinarily it is generally cylindrical in shape (although may be of other cross-sections square, triangular, etc.).

The term "palpation" means to feel with the hands and or fingers via pressure or other tactile sensations transmitted through the needle.

The term "percutaneously" means through the skin of a patient.

The term "pharmacological composition" means a solution or other mixture suitable for injection into a patient which is safe and effective.

The term "printed indicia" means words, text, images and or instructions, either verbatim or in meaning, on paper or other flexible media such as an instruction sheet, label and or package.

The term "proximal" means, in relative terms, in a direction towards the users (typically a physician), and generally means opposite of distal.

The term "radially inward" means, relatively, in a direction towards the center of something along a radius.

The term "radially outward" means, relatively, in a direction outward of the center of something along a radius.

The term "reduces patient pain" means lower the amount of pain experienced by a patient. This is sometimes measured on various scales, including various medically accepted pain scales.

The term "restrict penetration" means to cause a physical reaction forced to prevent, or at least make it palpably more difficult to penetrate.

The term "secondary axis" means an axis other than, non-parallel and non-collinear with another axis such as a major longitudinal axis.

The term "short of substantially penetrating" means less than a thickness or depth of something.

The term "slight proximal withdraw" means to move in a proximal direction a small distance, typically less than one centimeter.

The term "stopping" means to cease meaningful movement.

The term "stylet" means a medical device, or component thereof, which is generally elongated and extends through a lumen.

The term "surgically fixing bone position across said bone joint" means using one or more orthopedic implants and or biologics to help hold the position of one bone with respect to another. This may include mechanical fixation, as well as promoting bone fusion via bone chips, porous implants, proteins (bone morphogenetic and otherwise), cages, and the like.

The term "surgically sterile" means sufficiently devoid of biological pathogens such as to be suitable to insert or inject into a patient without material risk of causing infection.

Articles and phases such as, "the", "a", "an", "at least one", and "a first", are not limited to mean only one, but rather are inclusive and open ended to also include, optionally, multiple such elements. Likewise, "comprising" is open ended and inclusive.

The term "and/or" means, inclusively, both "and" (conjunctive) as well as "or" (disjunctively).

With reference to the drawing FIGS. 1A-9C, various examples are shown. For simplicity, systems are prefixed in the hundred's digit (e.g. systems and/or needles 200, 300, 400, 500, 900). The ten's digit and the one's digit in the reference characters of needles 200, 300, 400, 500, 900 generally correspond to similar features. Needle 900 in FIGS. 6A-9C generically representative of a needle, including needles 200, 300, 400, 500 and otherwise. They further show a method for anesthetizing nerves. The method may comprise inserting a needle, 200, 300, 400, 500, 900 percutaneously through the skin 707 (see FIGS. 7A and 7B), 810 (See FIG. 8) in a patient. The needle has a leading apex 250, 350, 450, 550 that is dulled to restrict penetration through articular cartilage 703, 704. The needle further has a needle wall 201, 301, 401, 501 surrounding a lumen 204, 304, 404, 504 extending from a proximal end 220, 320, 420, 520 to at least one opening 212, 312, 412, 512 near a distal end 213, 313, 413, 513 of the needle. The needle further may have during insertion means for blocking 230, 330, 430, 530, 902a, FIG. 2C, cartilage 703, 704, 803, 804 and/or bone tissue 701, 702 (FIG. 7C), 801, 802, I, S (FIG. 9A) from clogging the opening. The needle and its leading apex is advanced into a bone joint (see for example, FIGS. 7B, 8, 9).

The user, typically a doctor such as an anesthesiologist or otherwise, stops the needle leading apex short (see for example FIG. 7C) of substantially penetrating bone joint articular cartilage 703 and joint bone 701 while maintaining said opening in said bone joint. Optionally, this may be with the act of stopping said needle short comprises advancing said needle leading apex until palpation indicates contact with articular cartilage or bone, followed, optionally, by slight proximal withdraw (see for example FIGS. 7D, 7E) of said leading apex while the needle's opening in the bone joint. Moreover, unlike when the user gets proper needle penetration into the joint (see e.g. FIG. 7E), sometimes the needle initially may be advanced such that the leading apex contacts bone on one side of the joint, such as bone 701, outside of articular cartilage 703. In such case, a needle leading apex that is not dulled may well penetrate into the bone 701, and particularly through softer cancellous bone, leaving the distal end opening of the needle in the wrong place, outside of the joint. This may occur, for example. in an SI joint (see FIG. 9A). By having a dulled needle leading apex, this is reduced or eliminated.

The user injects through a lumen a pharmacological composition of matter comprising a local anesthetic 970b and out of the needle's opening (see for example FIG. 7F) and into the bone joint to contribute to the anesthetizing of nerves 706 near the bone joint. Optionally, the user may withdraw the means for blocking 230, 330, 430, 530, 902a from the needle's lumen prior to injecting. When such means for blocking comprises (an optional) stylet 230, 330, 430, 530 extendable along and within the needle's lumen, the needle examples with no stylet, such as for example if it is withdrawn from the lumen, are illustrated in FIGS. 2E, 3E, 4E, and 7D. This optionally may include having a needle comprises attachment means 532 at its proximal end, and comprising the act of attaching liquid injection means to said attachment means. Optionally, a hollow stylet within the needle's lumen and with its own lumen (to carry the injectables) may have its own side opening that could be rotated within the needle lumen to provide blocking or not (e.g. the two openings overlap. However, for simplicity, normally solid, withdrawable stylets are preferred when stylets are used.

Figure 3A:
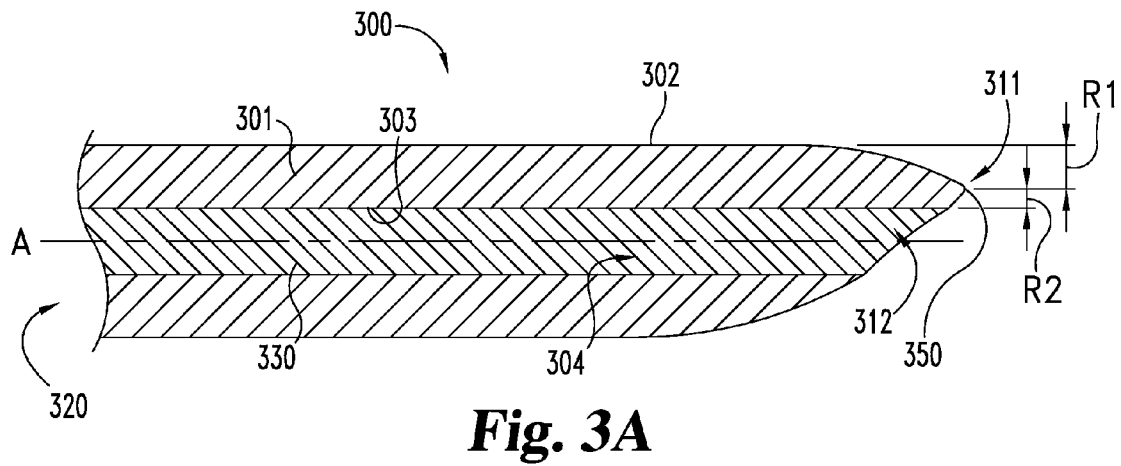
FIGS. 3A-3G show a second example of a the ends of needle, with 3A a full section view, 3B a side elevation view, 3C a front view, 3D like 3A but with a stylet partially withdrawn, 3E like 3A but without a stylet, and 3F (side) and 3G (distal end view) with the distal tip of the needle bent.
Figure 3B:
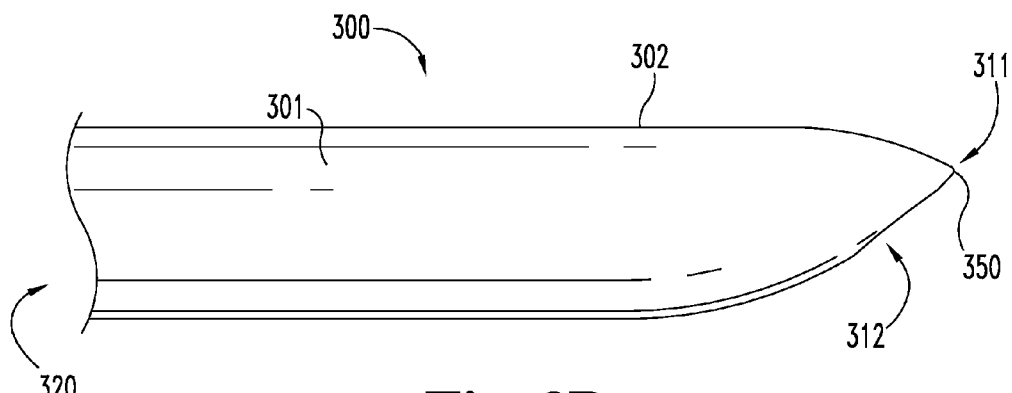
Figure 3C:
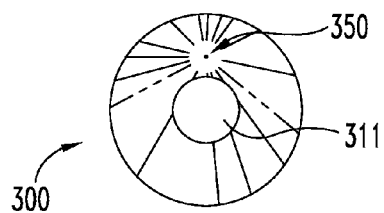
Figure 3D:
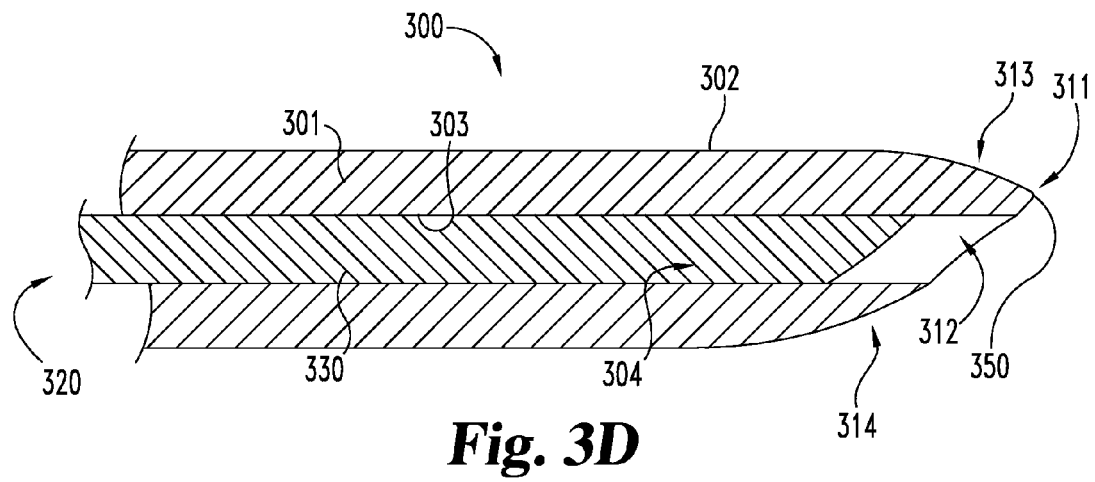
Figure 3E:
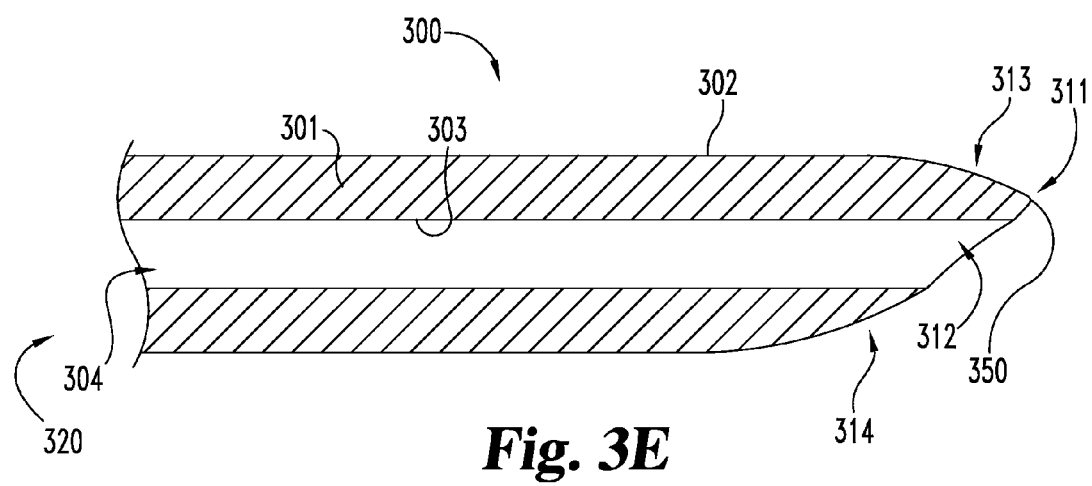
Figure 3F:
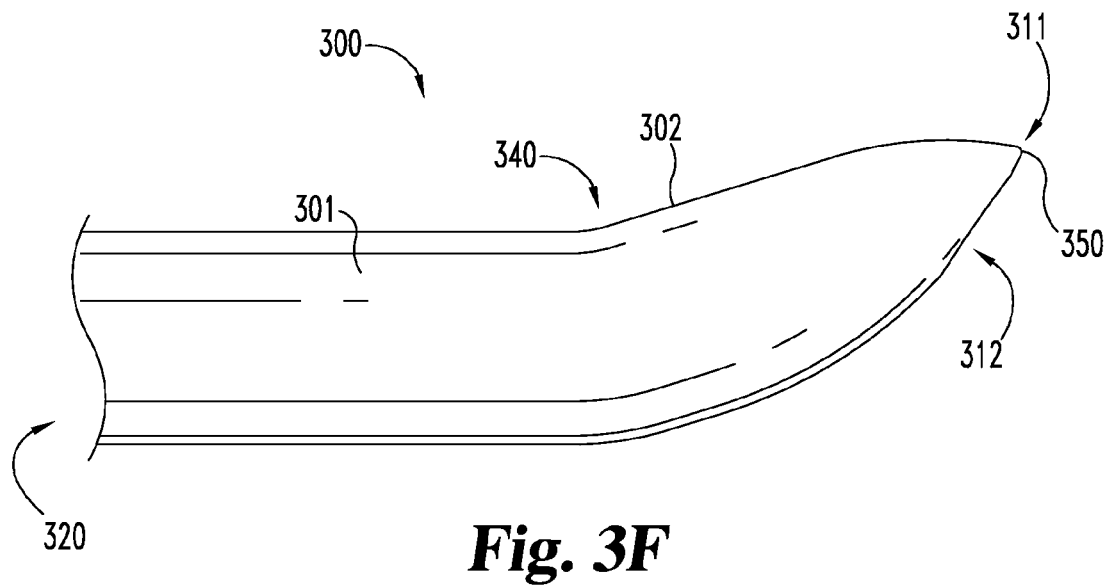
Figure 3G:
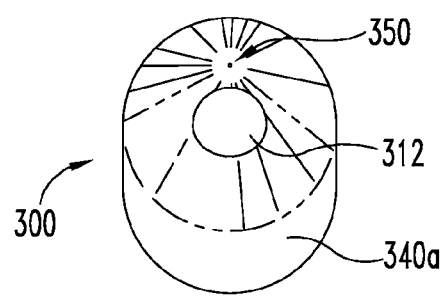
Figure 4A:
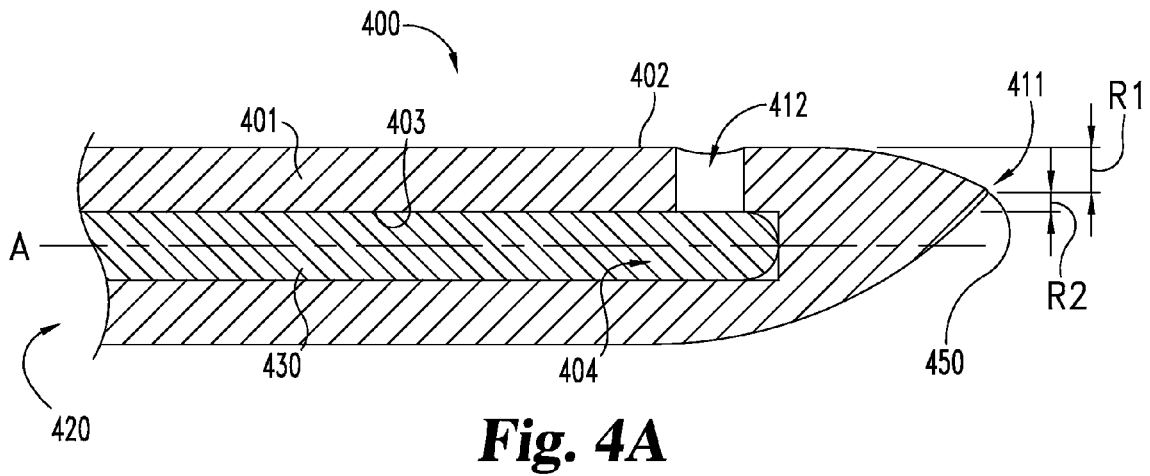
FIGS. 4A-4G show a third example of a the ends of needle, with 4A a full section view, 4B a side elevation view, 4C a front view, 4D like 4A but with a stylet partially withdrawn, 4E like 4A but without a stylet, and 4F (side) and 4G (distal end view) with the distal tip of the needle bent.
Figure 4B:
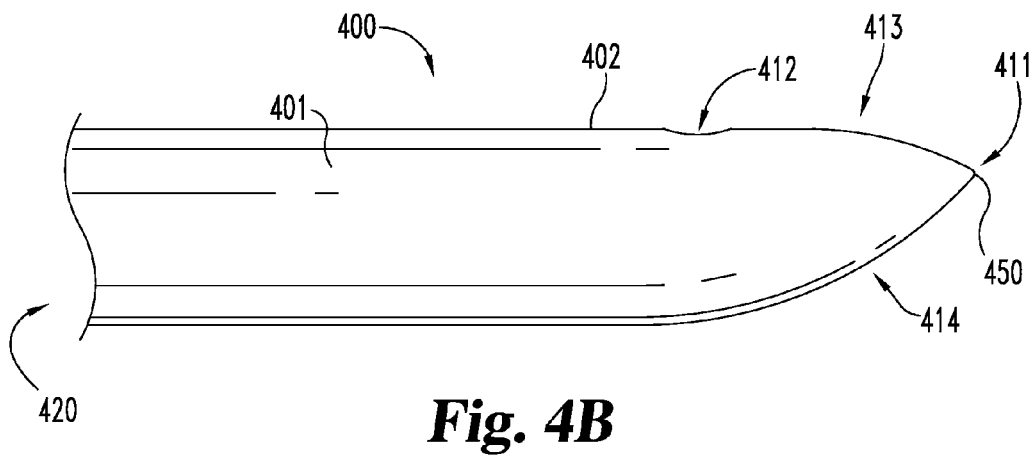
Figure 4C:
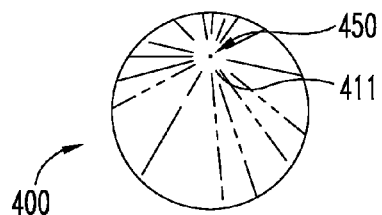
Figure 4D:
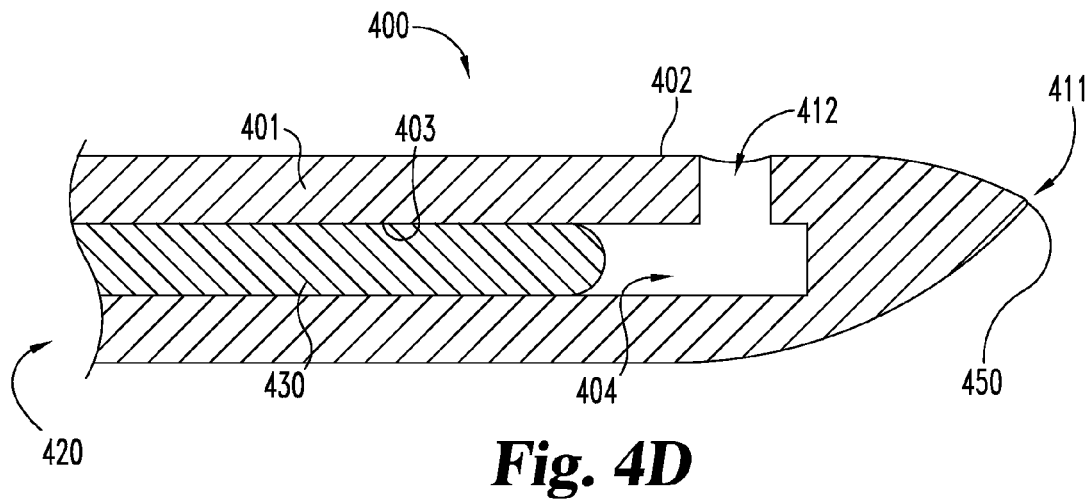
Figure 4E:
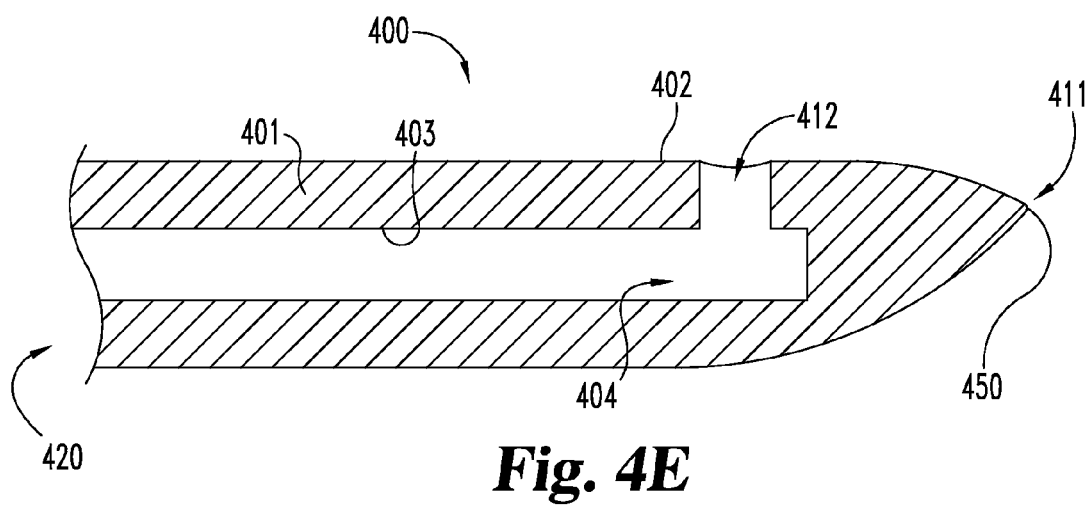
Figure 4F:
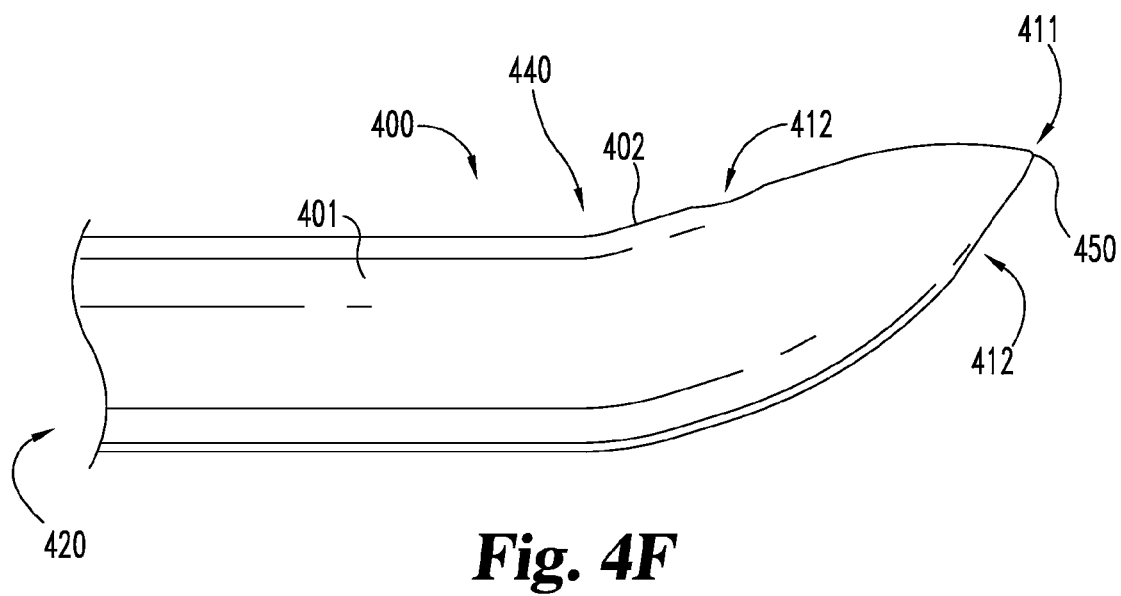
Figure 4G:
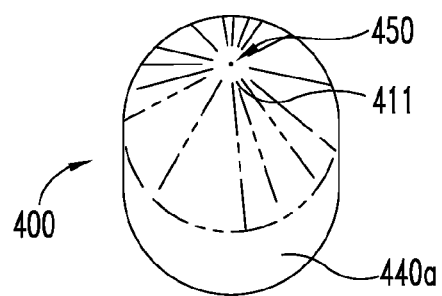

Also, optionally, but preferably, the user also injects through the lumen a pharmacological composition of matter comprising a contrast agent CM, 50a (see for example FIG. 7E) out of said opening and into the bone joint. Preferably, this optional act is done after the act of advancing the needle described above. Also, preferably, this optional injecting contrast media is done before injecting a pharmacological composition of matter comprising a local anesthetic. This may help confirm, by fluoroscope visualization or other technology corresponding to the contrast agent, that the needle and its opening are properly located. One advantage of the optional arrangement of FIGS. 2F and 2G, 3F and 3G, 4F and 4G and/or 5F and 5G is that the deflection allows, by rotation of the needle, to finely adjust (via movement of an eccentric opening around the arc of rotation) the location of the needle opening under visualization. This feature and advantage, to a somewhat lesser extent, may also be used with the axially offset leading apex versions, such as apex 350 and/or 450 (see for example. FIGS. 3A and 4A). Moreover, such bent variations and/or axially offset apex may enhance user steer ability by provide a skiing effect, whereby the underside 240a, 340a, 440a, 540a, when presented frontally to the cartilage and/or bone, tends to ski up on the articular cartilage and/or bone, rather than penetrate into it. This provides palpation to the user who may rotate the needle to advance in the joint without such penetration.

Note that injecting (local anesthesia and/or contrast media) may be accomplished by any force, such as in the two drawn examples of a syringe 970a (see for example FIG. 7F), catheter and bulb 50 (see for example FIG. 7E) and/or otherwise, with them being attached to the proximal end of the needle.

One optional use is in diagnosis, such as diagnosing whether the anesthetizing of nerves near said bone joint reduces patient pain in a collateral region. This is normally done with the patient conscious and giving responses regarding pain and pain levels after the local anesthesia.

If the diagnosis is positive, therapy may follow (immediately or later an another procedure). For example, such therapy may the act of surgically fixing bone position across a bone joint. This may be any such surgery in the field of orthopedics for or at a bone joint. As but one example only, this might include where bone joint is a sacroiliac joint, and the pain in a collateral region is lower back pain. Therapeutic treatment may also (and/or instead of) employ injectables via the present needle, including for example steroids, stem cells, glucose, hyaluronidase, and/or otherwise.

Optionally, the needle may have one or more various features. For examples, as shown in FIGS. 3A-3G and 4A-4G, the needle leading apex 350, 450 is located both radially inward R1 of an outer surface 302, 402 of said needle and radially outward R2 of an inner surface 303 (and radially outward of axis A), 403 of the lumen along a common radius. This provides, as shown, the leading apex is neither a sharp cartilage or bone cutting edge or point at the outer surface nor the inner surface.

Figure 9A:
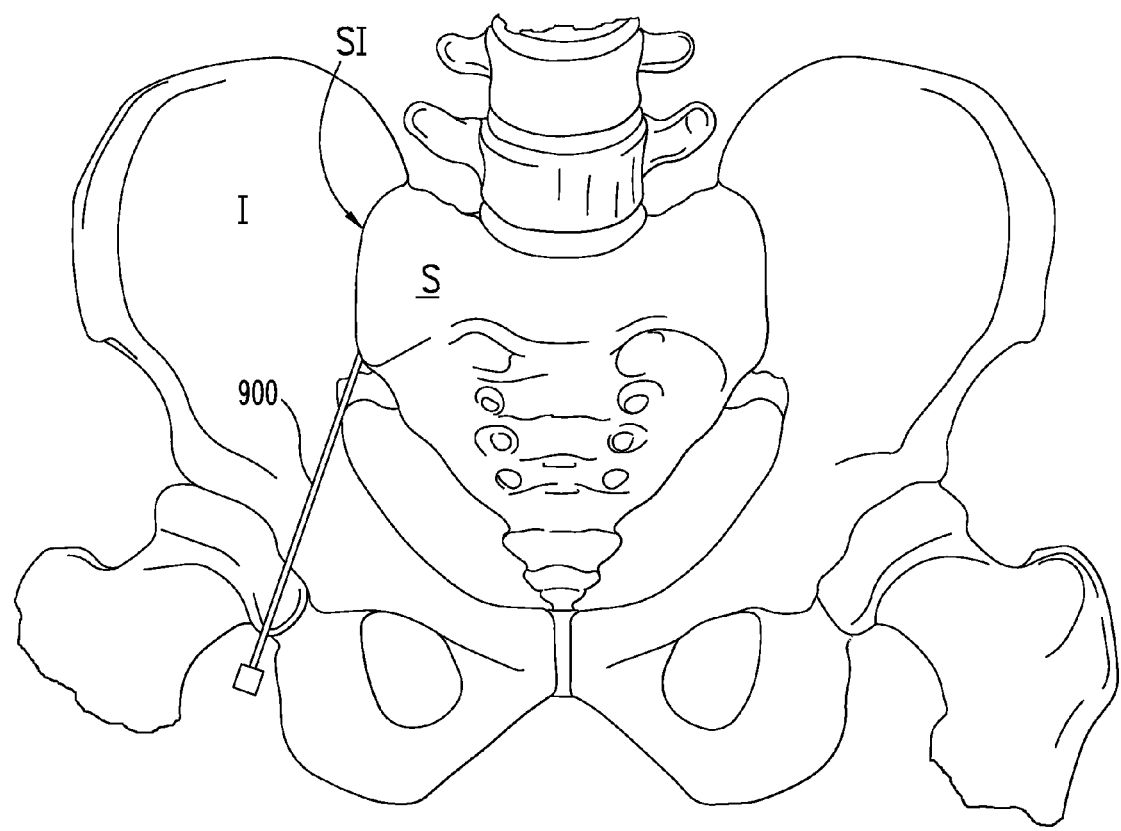
FIGS. 9A, 9B and 9C shows other example methods in an S-I joint.
Figure 9B:
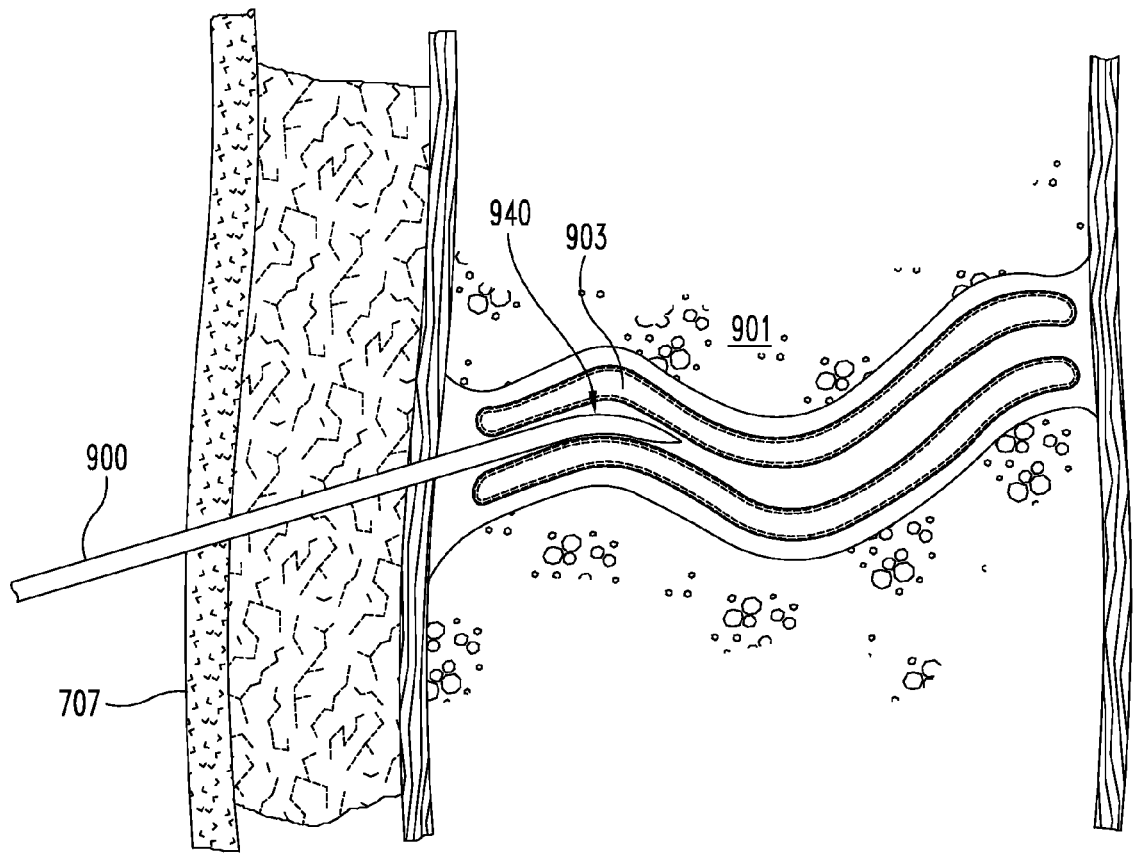
Figure 9C:
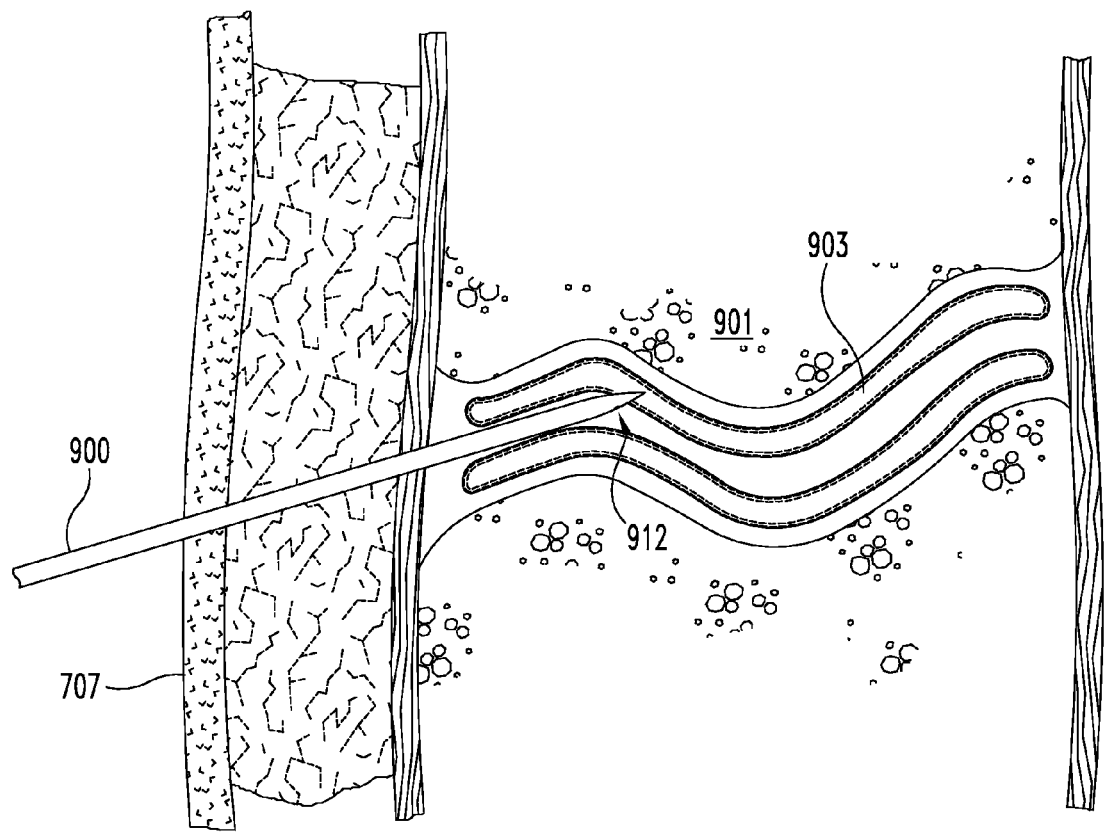

Another optional feature is exemplified in FIGS. 2F-2G, 3F-3G, 4F-4G and/or 5F-5G, with the needle has a major longitudinal axis A, and wherein the needle is deflected off said longitudinal axis A at its distal end along a secondary axis B an amount less than about thirty degrees (measured by the acute angle between them). The arrangement may optionally be used with any of the needles shown or described. It is also shown in FIG. 9B. Such deflection may be with a curve or bend 240, 340, 440, 540, 940. The needle may optionally be manufactured with this feature prior to being placed in a container or kit, or optionally a user could impart the bend at or before surgery (with or without instructions on the printed indicia regarding such bending). Note also that the needle of FIGS. 2A-2E has its opening 212 (or optionally more than one such opening, such as openings 212a and 212b) transverse to the lumen. This is with the distal end view (FIG. 2C) without much or any of the opening presented, thereby having that frontal presentation of surface(s) to the cartilage and/or bone not present the opening for clogging, but rather the opening 912 (see for example FIG. 9C) may be substantially shielded, thereby being another example of means for blocking cartilage and/or bone tissue from clogging the opening. This is the case with or without an optional stylet which also may provide, or at least enhance, such blocking.

Figure 5A:
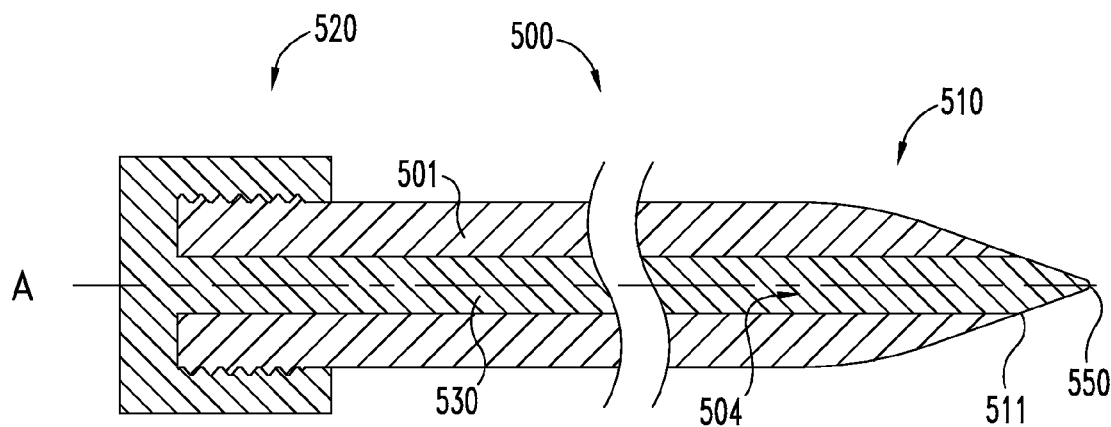
FIGS. 5A-5G show a fourth example of a the ends of needle, with 5A a full section view, 5B a side elevation view, 5C a front view, 5D like 5A but with a stylet partially withdrawn, 5E like 5A but without a stylet, and 5F (side) and 5G (distal end view) with the distal tip of the needle bent.
Figure 5B:
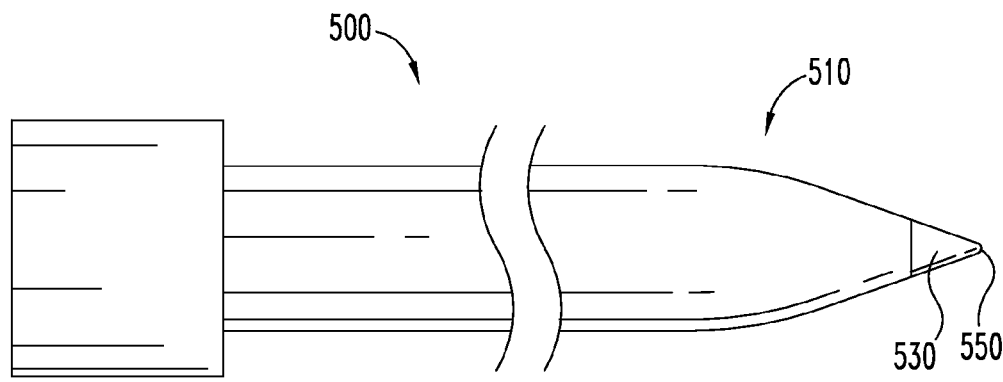
Figure 5C:
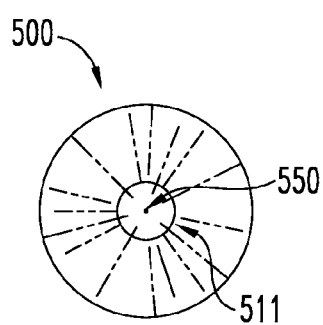
Figure 5D:
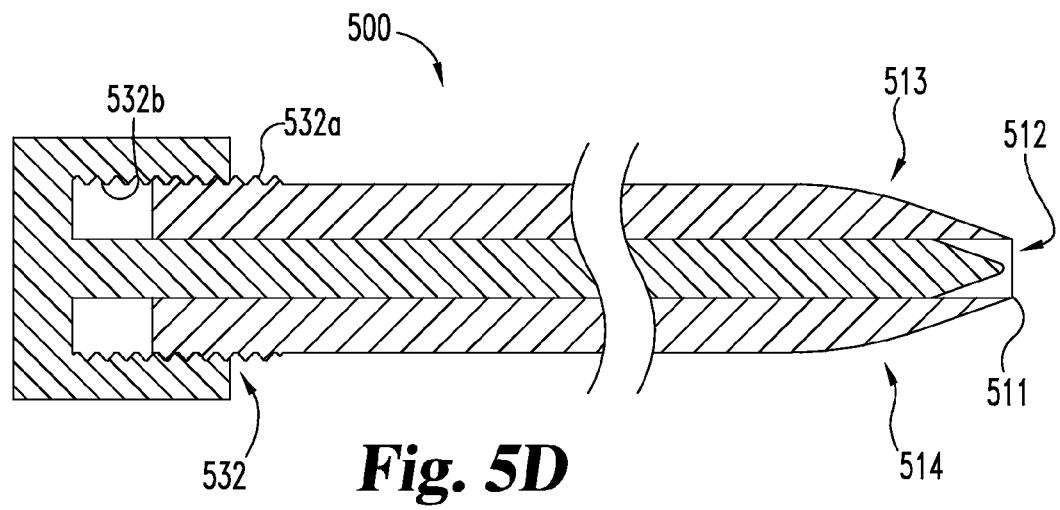
Figure 5E:
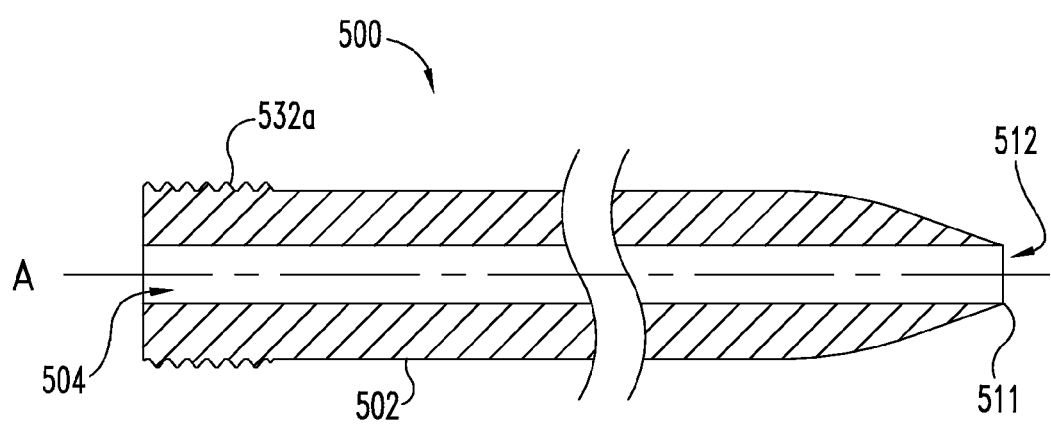
Figure 5F:
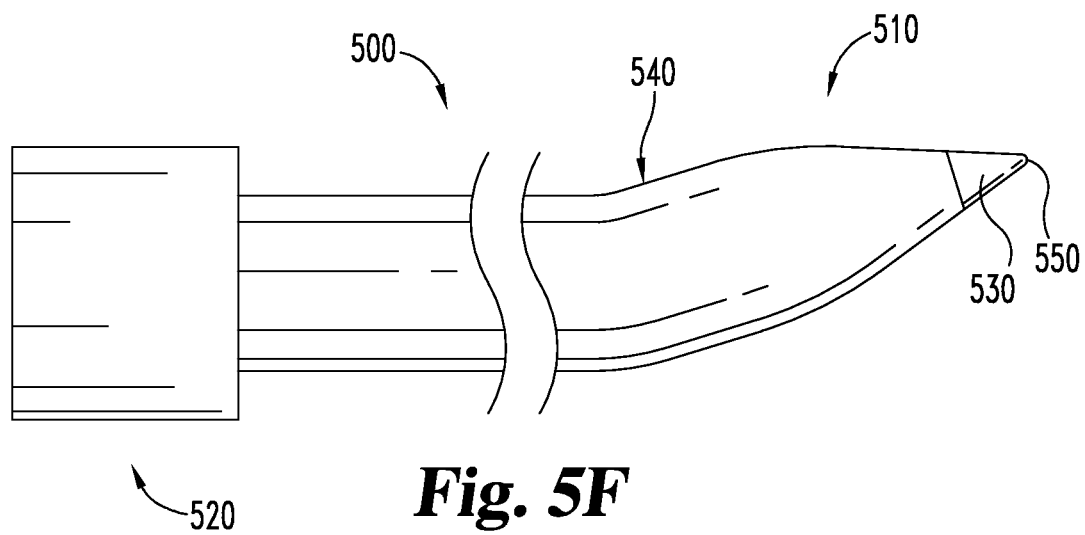
Figure 5G:
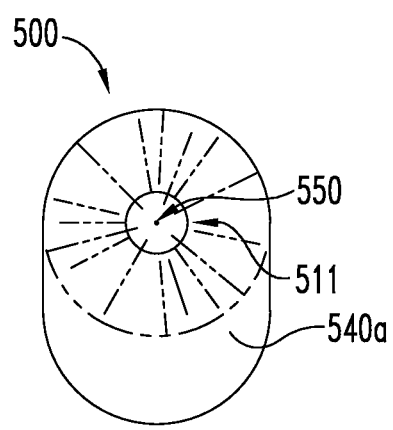

The needle apex may be the distal part of the outer needle (see for example at 311, 411, 511). This is at the convergence of one or more tapered sides, such as first tapers 213, and such as second tapers 214. The needle apex may also be on the stylet, at least in some positions (FIGS. 5A-5G) and the distal part of the outer needle, such as circuitous edge 511 (FIGS. 5A-5G) in other positions, such as with the stylet partially withdrawn (FIG. 5D) or absent (FIG. 5E). Such tapers may be flat, curved, convex, concave, frusto-conical, and/or otherwise. Dulling is present in all of the illustrated apex embodiments. Optionally, trailing edges may be dulled and/or may be sharp corners.

Another optional feature of a needle comprises attachment means 532 at its proximal end. This may be any such means as defined, and for example the drawing FIGS. 5D and 5E show a male thread 532a on the needle and a female thread 532b in an outer cap or housing of the stylet. This may hold the stylet in place in the lumen. It optionally allows for partial withdrawal, such as unscrewing threaded (proximal end) to cause corresponding withdrawal of the stylet wholly or partially within the needle lumen opening, as illustrated in comparing FIGS. 2A and 2D, 3A and 3D, 4A and 4D, and 5A and 5D.

Figure 6A:
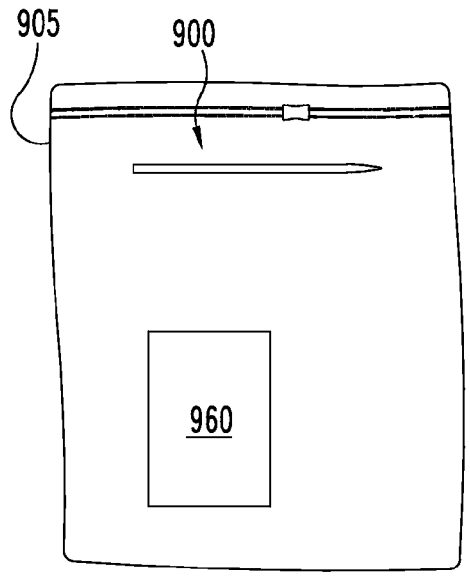
FIGS. 6A-6D show various examples of kits.
Figure 6B:
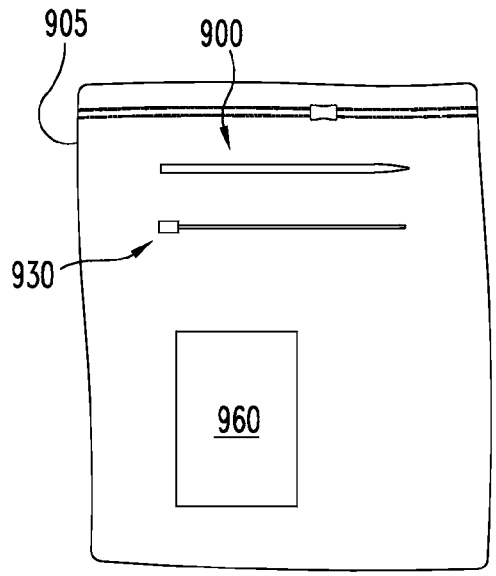
Figure 6C:
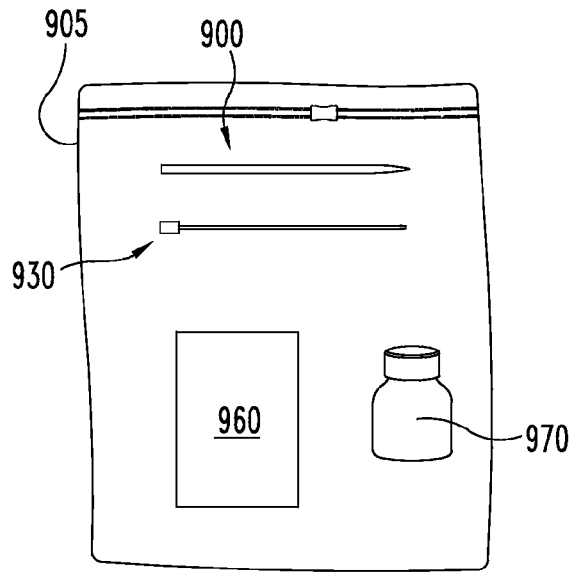

A kit may be provided. FIGS. 6A-6D illustrate some examples. FIG. 6A includes container 905, needle 900 and printed indicia 960. Optionally, the printed indicia may include at least one medical indication regarding the application of local anesthesia. Such medical indication may be for application within a bone joint and/or other indications. Such medical indication may be for therapeutic treatment with injectables via the present needle, including for example steroids, stem cells, glucose, hyaluronidase, and/or otherwise, and/or for fusion of a joint via orthopedic implant. FIG. 6B is similar to FIG. 6A, adding stylet 930. FIG. 6C is similar as well, further including a sub-container containing a pharmacological local anesthesia 970 composition of matter in liquid form. This may be a bottle, vial, syringe or otherwise.

Figure 6D:
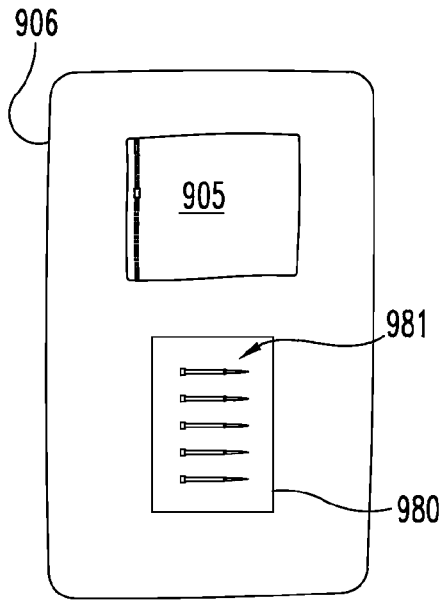
Figure 7A:
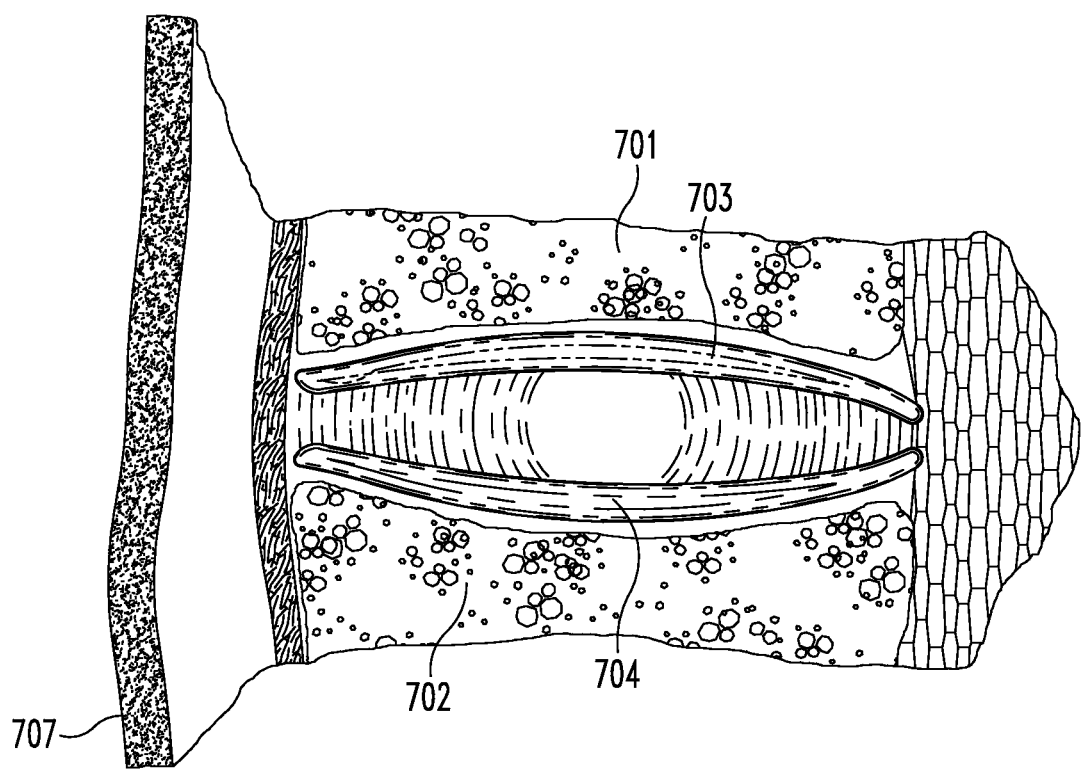
FIGS. 7A-7F show, in sequence, an example method using a needle.
Figure 7B:
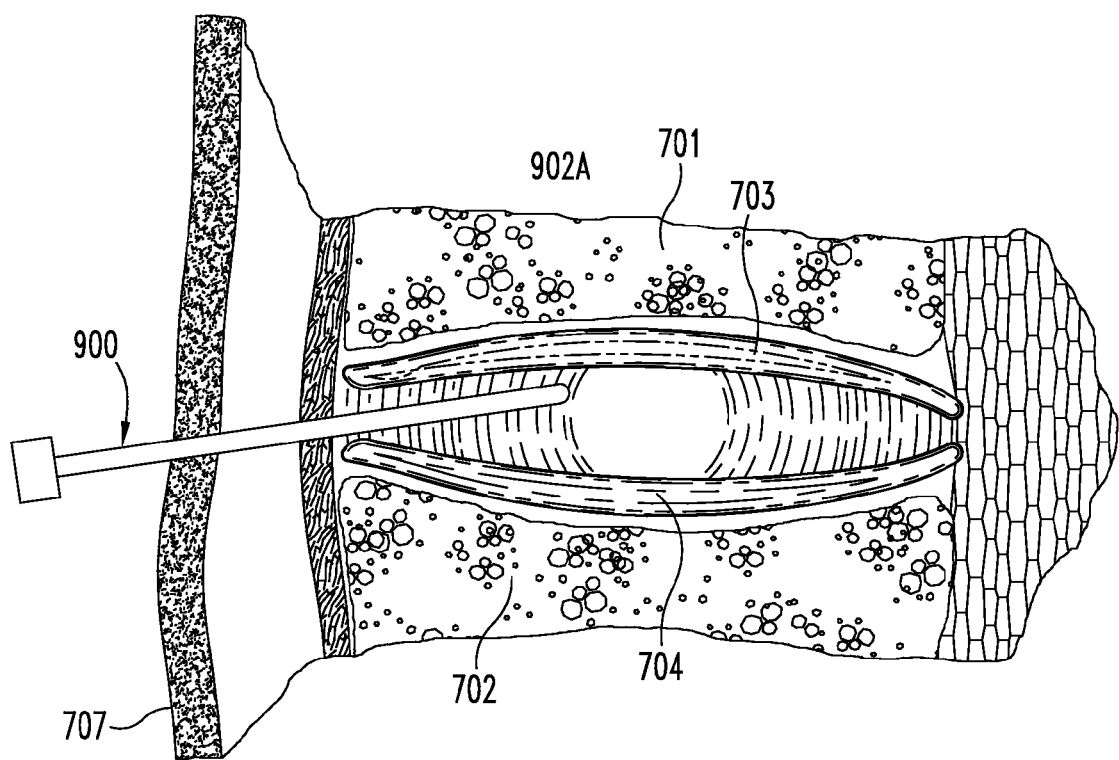
Figure 7C:
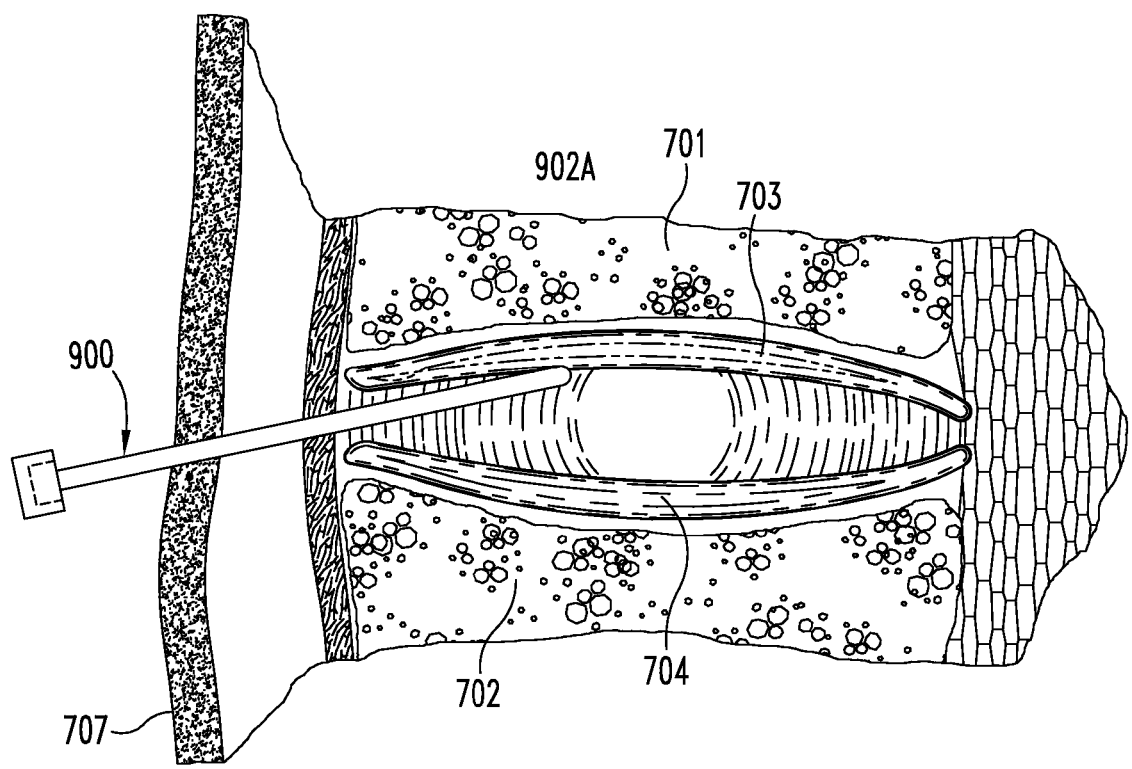
Figure 7D:
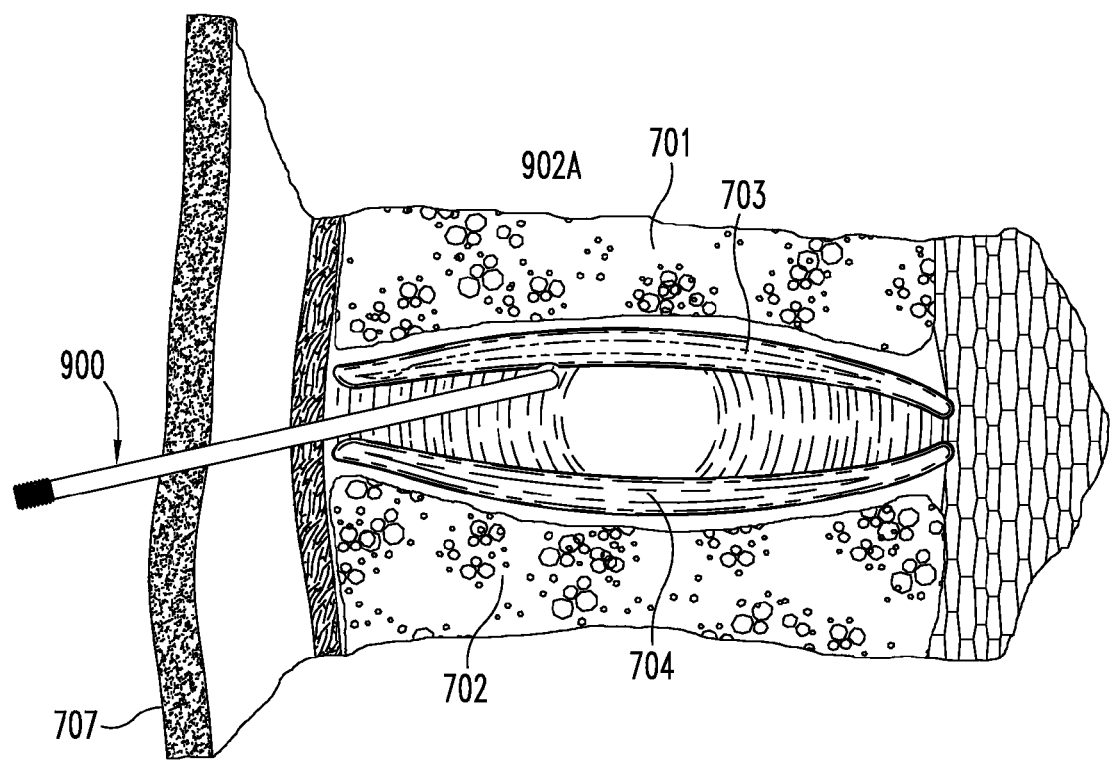
Figure 7E:
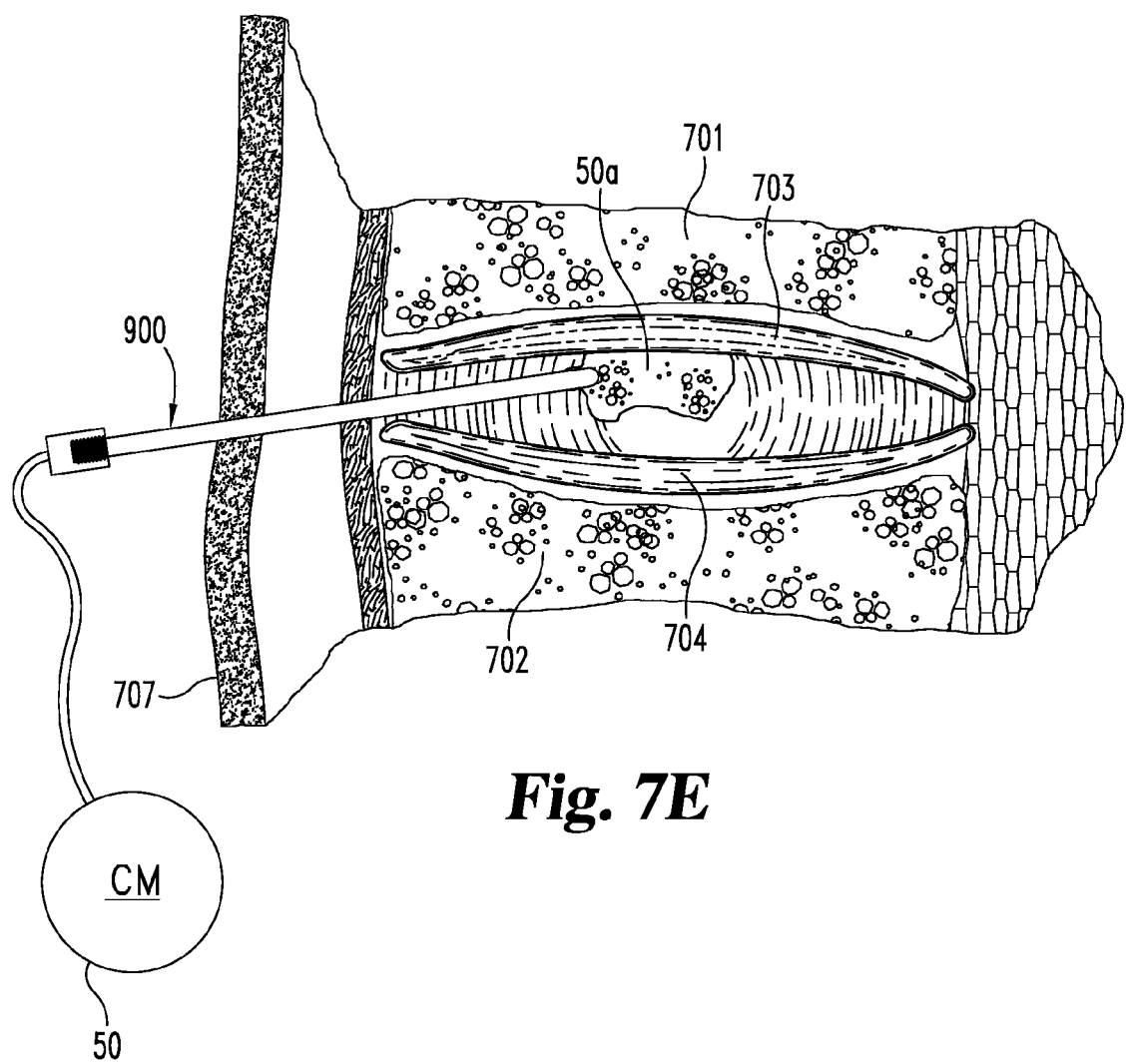
Figure 7F:
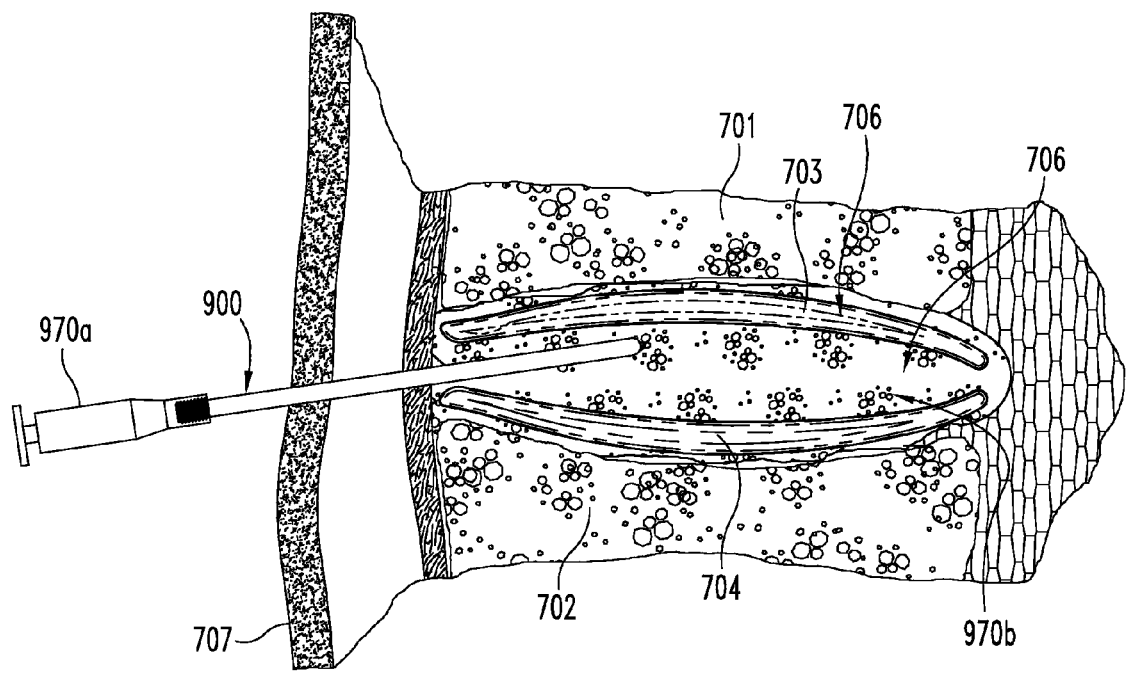
Figure 8:
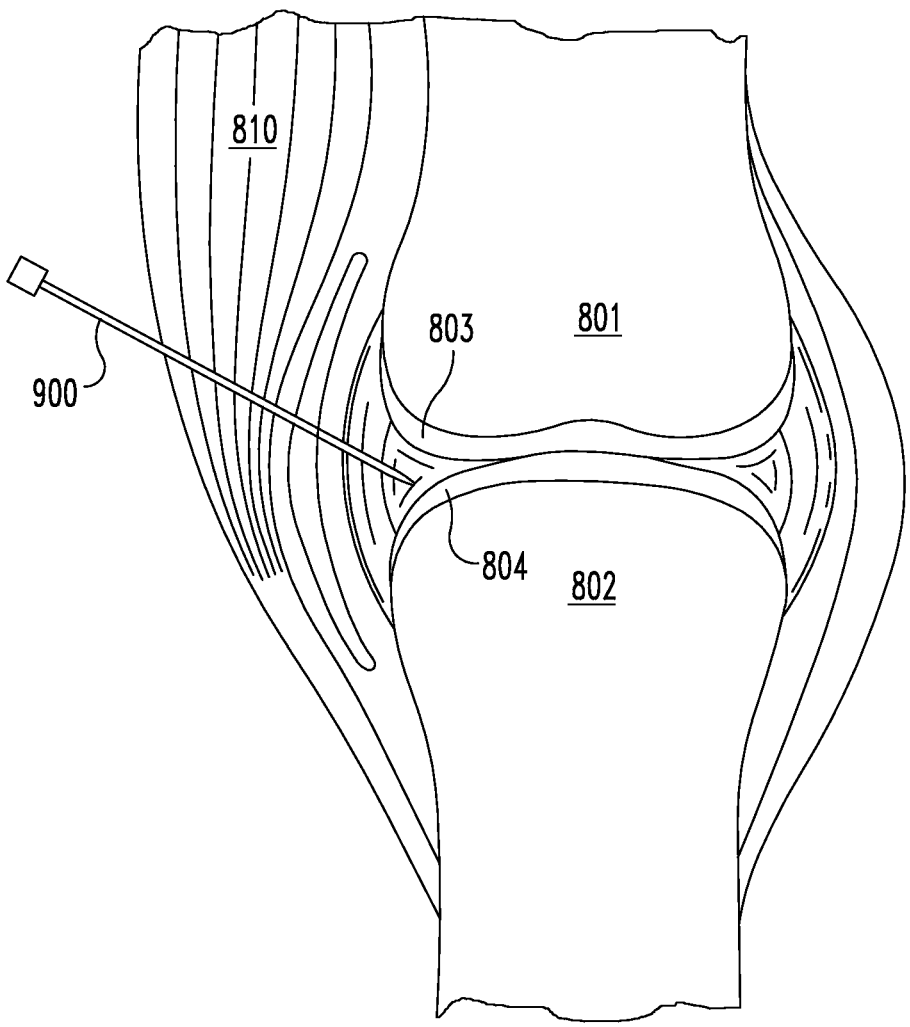
FIG. 8 shows another example method.

A kit, such as shown in FIG. 6D, may comprise one or more of the above and at least one orthopedic implant 981 (in a container 980 or not) for fixing bone position at a bone joint. As but one example, such implants 981 may be an orthopedic screw and/or that or other orthopedic implant adapted for fixation of a sacroiliac joint. This kit may include a container 906 for housing the at least one orthopedic implant 981 with or without respective container 980 and/or the container 905.

With or without a kit, the needles 200, 300, 400, 500, 900 may be provided separately and/or with or without a stylet.

The needles may be any length and/or diameter (gauge) medically suitable. For example, typically the overall needle length will be between about 1.5 inches and 6 inches, and optionally with about 3.5 inch length being one choice. The diameter typically with be between about 18 gauge and 25 gauge. Other sizes are possible as well.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A method for anesthetizing nerves, comprising the acts of:
   inserting a needle percutaneously in a patient, said needle having a lumen with a stylet therein, said stylet or said needle and said stylet collectively form a leading apex that is dulled to restrict penetration through articular cartilage, said needle further having said lumen extending from a proximal end to at least one opening at or near a distal end of said needle, said needle further having during insertion blocking means comprising a distal portion of said stylet at said needle opening for blocking cartilage and/or bone tissue from clogging said opening, said needle further comprises attachment means at its proximal end, said attachment means configured to hold said stylet in position during insertion, and wherein during insertion said needle is axially rotated to cause deflection to aid in traversal of the sacroiliac joint;
   advancing said needle leading apex into the sacroiliac joint lumen between layers of articular cartilage until palpation indicates contact with articular cartilage or bone;
   withdrawing said stylet while maintaining said opening in the sacroiliac joint lumen; and
   injecting through said lumen a pharmacological composition of matter comprising a local anesthetic and out of said opening and into the sacroiliac joint to contribute to the anesthetizing of nerves near the sacroiliac joint, wherein said pharmacological composition passes through the opening at or near the distal end of the needle.

2. The method of claim 1 comprising the act of attaching liquid injection means to said attachment means.

3. The method of claim 2 wherein said attachment means comprises screw threads.

4. The method of claim 3 wherein said leading apex is said stylet.

5. The method of claim 1 and further comprising the act of diagnosing whether the anesthetizing of nerves near the sacroiliac joint reduces patient pain in a collateral region.

6. The method of claim 5 and further comprising the act of surgically fixing bone position across the sacroiliac joint.

7. The method of claim 6 wherein the pain in a collateral region is lower back pain.

8. The method of claim 6 wherein said needle leading apex is located both radially inward of an outer surface of said needle and radially outward of an inner surface of said lumen along a common radius.

9. The method of claim 1 wherein said needle has a major longitudinal axis, and wherein said needle is deflected off said longitudinal axis at its distal end along a secondary axis an amount less than about thirty degrees.

10. The method of claim 1 and further comprising the act of withdrawing said blocking means from said lumen prior to the act of injecting.

11. The method of claim 1 and further comprising the act of injecting through said lumen a pharmacological composition of matter comprising a contrast agent out of said opening and into the sacroiliac joint after said act of advancing said needle and before said act of injecting a pharmacological composition of matter comprising a local anesthetic.

12. The method of claim 1 wherein said leading apex is said stylet.

13. The method of claim 1 further comprising the step of: rotating said needle within the sacroiliac joint.

* * * * *